US012478718B2

(12) United States Patent
Penka et al.

(10) Patent No.: US 12,478,718 B2
(45) Date of Patent: Nov. 25, 2025

(54) REGULATING BLOOD FLOW IN EXTRACORPOREAL CIRCULATION

(71) Applicant: LivaNova Deutschland GmbH, Munich (DE)

(72) Inventors: Ottmar Penka, Munich (DE); Friedemann Schubert, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 488 days.

(21) Appl. No.: 17/942,532

(22) Filed: Sep. 12, 2022

(65) Prior Publication Data

US 2023/0001067 A1 Jan. 5, 2023

Related U.S. Application Data

(63) Continuation of application No. PCT/EP2020/060271, filed on Apr. 9, 2020.

(51) Int. Cl.
*A61M 1/36* (2006.01)

(52) U.S. Cl.
CPC ........ *A61M 1/3627* (2013.01); *A61M 1/3623* (2022.05); *A61M 1/3639* (2013.01); *A61M 1/3626* (2013.01)

(58) Field of Classification Search
CPC .............. A61M 1/3627; A61M 1/3623; A61M 1/3639; A61M 1/3626; A61M 60/109;
(Continued)

(56) References Cited

U.S. PATENT DOCUMENTS

2004/0184953 A1* 9/2004 Litzie .................. A61M 60/232 604/6.14
2006/0089586 A1* 4/2006 Kaus .................. A61M 1/3666 604/4.01

(Continued)

FOREIGN PATENT DOCUMENTS

EP 2823833 A1 1/2015
EP 3050584 A1 8/2016

(Continued)

OTHER PUBLICATIONS

International Search Report and Written Opinion for International Application No. PCT/EP2020/060271, date mailed Oct. 29, 2020.

(Continued)

*Primary Examiner* — Kai H Weng
*Assistant Examiner* — Kate Elizabeth Strachan
(74) *Attorney, Agent, or Firm* — Seager, Tufte & Wickhem LLP

(57) ABSTRACT

A system for regulating blood flow in extracorporeal circulation, and including a blood reservoir to receive blood from a patient, an oxygenator to condition the blood, a centrifugal pump to pump the blood from the blood reservoir to the oxygenator and back to the patient, an electronic remote clamp to regulate flow of the blood, and a controller to operate in a flow control mode and a speed control mode. The controller includes an operational element to set a blood flow value in the flow control mode and to set a speed of the centrifugal pump in the speed control mode. The controller to automatically switch between the flow control mode and the speed control mode in response to one or more trigger conditions and to automatically switch between the speed control mode and the flow control mode in response to opening the electronic remote clamp.

20 Claims, 3 Drawing Sheets

(58) Field of Classification Search
CPC .. A61M 60/232; A61M 60/38; A61M 60/523; A61M 60/531; A61M 2205/18; A61M 2205/3334; A61M 2205/3386; A61M 1/3667
See application file for complete search history.

(56) References Cited

U.S. PATENT DOCUMENTS

| | | | | |
|---|---|---|---|---|
| 2008/0171960 | A1* | 7/2008 | Brieske | A61M 1/3626 604/4.01 |
| 2011/0208107 | A1* | 8/2011 | Muller-Spanka | A61M 1/3693 604/6.11 |
| 2018/0344912 | A1* | 12/2018 | Turner | A61M 60/523 |
| 2021/0268260 | A1 | 9/2021 | Penka et al. | |

FOREIGN PATENT DOCUMENTS

| | | | |
|---|---|---|---|
| JP | H10132641 | A | 5/1998 |
| JP | 2006325750 | A | 12/2006 |
| JP | 2020025816 | A | 2/2020 |
| WO | 2013132923 | A1 | 9/2013 |
| WO | 2019181658 | A1 | 9/2019 |

OTHER PUBLICATIONS

Third Party Observation for International Application No. PCT/EP2020/060271, Date of Submission, Aug. 9, 2022.

* cited by examiner

REGULATING BLOOD FLOW IN EXTRACORPOREAL CIRCULATION

CROSS REFERENCE TO RELATED APPLICATIONS

This application is a continuation of International Application No. PCT/EP2020/060271, filed Apr. 9, 2020, the disclosure of which is incorporated herein by reference.

TECHNICAL FIELD

The present disclosure relates to extracorporeal circulation. More specifically, the present disclosure relates to regulating the flow of blood in extracorporeal circulation.

BACKGROUND

Usually, the main blood pump in a heart lung machine (HLM) is either a roller pump or a centrifugal pump. Roller pumps are occlusive, such that the speed of a roller pump, which may be measured in revolutions per minute (RPMs), linearly corresponds to the flow rate of the blood. In a roller pump, the relation between speed and blood flow depends only on the cross-sectional area of the pump's tubing segment. Centrifugal pumps are non-occlusive, such that the speed of the centrifugal pump does not linearly correspond to the flow rate of the blood. Instead, the flow rate depends on the resistance in the tubing (e.g., of the oxygenator and filters) and on the patient's systemic resistance. For this reason, a centrifugal pump in an HLM is associated with a flow sensor for measuring the actual flow rate of the blood and an electronic remote clamp (ERC) that is used to clamp the blood flow line (e.g., tubing) and stop the flow of blood whenever needed, such as to prevent blood from flowing in the retrograde or wrong direction.

Typically, a centrifugal pump is operated in one of two control modes that is selectable by manually activating a button or switch. One button activates a flow control mode and the other button activates a speed control mode. Manually switching from one mode to the other can be done at any time during pump operation. Also, the control system of a centrifugal pump contains a control knob for manually increasing or decreasing the flow rate in flow control mode and for manually increasing or decreasing the speed of the pump in speed control mode. In addition, the control system may include an ERC-close button to manually close the ERC, and an ERC-open button to manually open the ERC.

The flow control mode allows the user to set a flow rate that the centrifugal pump maintains by automatically changing the speed of the pump according to changes of hydraulic resistance in the fluid circuit, i.e., increasing the speed if the resistance increases and decreasing the speed if the resistance decreases. The speed control mode allows the user to set a pump speed, such as measured in RPMs, that is kept constant and results in flow rate changes in response to changes in the hydraulic resistance in the fluid circuit, i.e., the flow rate decreases with increasing resistance and increases with decreasing resistance.

Often, in operation, the centrifugal pump is kept in flow control mode to maintain a constant flow rate during extracorporeal circulation of the blood. The HLM includes multiple sensors, such that if a signal from one or more of these sensors is not within a normal range a trigger condition is generated and the system reacts to provide safe operating conditions.

In response to some trigger conditions, the ERC is closed to stop the flow of blood and the centrifugal pump is slowed to a speed that prevents retrograde blood flow after the trigger condition has been cleared and the ERC opened. Also, after clearing the trigger condition, the HLM is manually switched to speed control mode by pushing the corresponding button, the speed of the centrifugal pump is manually increased by turning the control knob, and the ERC is manually opened by pushing the ERC-open button. After these steps have been taken, the HLM is manually switched back to flow control mode by pushing another button to resume constant flow operations. Thus, operating the HLM requires a user to perform a relatively complicated sequence of steps, which may result in wrong maneuvers and put the patient at risk.

SUMMARY

As recited in examples, Example 1 is a system for regulating blood flow in extracorporeal circulation. The system includes a blood reservoir configured to receive blood from a patient, an oxygenator configured to condition the blood from the patient, a centrifugal pump fluidly coupled to the blood reservoir and the oxygenator and configured to pump the blood from the blood reservoir through blood flow lines (e.g., tubing) to the oxygenator and back to the patient, an electronic remote clamp coupled to the blood flow lines and configured to regulate flow of the blood back to the patient, and a controller configured to operate in a flow control mode and a speed control mode. The controller including an operational element configured to set a blood flow value in the flow control mode and to set a speed of the centrifugal pump in the speed control mode, where the controller is configured to automatically switch between the flow control mode and the speed control mode in response to one or more trigger conditions and to automatically switch between the speed control mode and the flow control mode in response to opening the electronic remote clamp.

Example 2 is the system of Example 1, wherein the controller is configured to automatically close the electronic remote clamp, reduce the speed of the centrifugal pump, and switch operation from the flow control mode to the speed control mode in response to the one or more trigger conditions.

Example 3 is the system of Example 2, wherein the one or more trigger conditions indicate one of a retrograde blood flow condition, air bubbles in the blood, and a blood level in the blood reservoir.

Example 4 is the system of Example 3, wherein the controller is configured to receive signals from a blood flow sensor, an air bubble sensor, and a blood level sensor and to provide the one or more trigger conditions based on the blood flow sensor, the air bubble sensor, and the blood level sensor.

Example 5 is the system of Example 1, wherein if the one or more trigger conditions is based on blood level in the blood reservoir, the controller is configured to automatically increase the speed of the centrifugal pump after the one or more trigger conditions ends and to automatically begin opening the electronic remote clamp in response to reaching a speed threshold for the speed of the centrifugal pump.

Example 6 is the system of Example 5, wherein the controller is configured to continue opening the electronic remote clamp and, after a predetermined period, automatically switch from the speed control mode to the flow control mode.

Example 7 is the system of Example 1, wherein if the one or more trigger conditions is based on at least one of a retrograde blood flow and air bubbles in the blood, the speed of the centrifugal pump is changed by user manipulation of the operational element and the electronic remote clamp begins to open in response to the speed of the centrifugal pump reaching a speed threshold, such that the controller is configured to control the centrifugal pump and the electronic remote clamp in response to user manipulation of the operational element.

Example 8 is the system of Example 7, wherein the controller is configured to continue opening the electronic remote clamp and, after a predetermined period, automatically switch from the speed control mode to the flow control mode.

Example 9 is a system for regulating blood flow in extracorporeal circulation. The system including a blood reservoir configured to receive blood from a patient, a centrifugal pump fluidly coupled to the blood reservoir and configured to pump the blood from the blood reservoir through blood flow lines back to the patient, an electronic remote clamp coupled to the blood flow lines and configured to regulate flow of the blood back to the patient, and a controller configured to operate in a flow control mode and a speed control mode. Where the controller is configured to automatically close the electronic remote clamp and reduce the speed of the centrifugal pump and switch between the flow control mode and the speed control mode in response to one or more trigger conditions, and to automatically begin opening the electronic remote clamp in response to the speed of the centrifugal pump being increased to a speed threshold.

Example 10 is the system of Example 9, wherein the controller is configured to continue opening the electronic remote clamp and, after a predetermined period, automatically switch between the speed control mode and the flow control mode.

Example 11 is the system of Example 9, wherein if the one or more trigger conditions is based on blood level in the blood reservoir, the controller is configured to automatically increase the speed of the centrifugal pump to the speed threshold after the one or more trigger conditions ends.

Example 12 is the system of Example 9, including an operational element configured to set a blood flow value in the flow control mode and to set a speed of the centrifugal pump in the speed control mode. Where if the one or more trigger conditions is based on at least one of a retrograde blood flow and air bubbles in the blood, the speed of the centrifugal pump is increased to the speed threshold by user manipulation of the operational element.

Example 13 is the system of Example 9, including an oxygenator configured to condition the blood from the patient, wherein the centrifugal pump is fluidly coupled to the blood reservoir and the oxygenator and configured to pump the blood from the blood reservoir through blood flow lines to the oxygenator and back to the patient.

Example 14 is a method of regulating blood flow in an extracorporeal circulation system. The method including receiving blood, from a patient, in a blood reservoir, pumping the blood from the blood reservoir through blood flow lines to an oxygenator and back to the patient using a centrifugal pump, regulating flow of the blood back to the patient using an electronic remote clamp coupled to the blood flow lines, and controlling, using a controller, the centrifugal pump and the electronic remote clamp to operate in a flow control mode and a speed control mode. Where controlling the centrifugal pump and the electronic remote clamp includes automatically switching between the flow control mode and the speed control mode in response to one or more trigger conditions, and automatically switching between the speed control mode and the flow control mode in response to opening the electronic remote clamp.

Example 15 is the method of Example 14, including automatically closing the electronic remote clamp and automatically reducing the speed of the centrifugal pump in response to the one or more trigger conditions.

Example 16 is the method of Example 14, including receiving signals from a blood flow sensor, an air bubble sensor, and a blood level sensor and providing the one or more trigger conditions based on the signals from the blood flow sensor, the air bubble sensor, and the blood level sensor.

Example 17 is the method of Example 14, including automatically increasing the speed of the centrifugal pump after the one or more trigger conditions ends and automatically opening the electronic remote clamp in response to reaching a speed threshold for the speed of the centrifugal pump, if the one or more trigger conditions is based on blood level in the blood reservoir.

Example 18 is the method of Example 17, including the opening of the electronic remote clamp and, after a predetermined period, automatically switching between the speed control mode and the flow control mode.

Example 19 is the method of Example 14, including using an operational element to set a blood flow value in the flow control mode and to set a speed of the centrifugal pump in the speed control mode, and changing the speed of the centrifugal pump to reach a speed threshold for the speed of the centrifugal pump by manually manipulating the operational element and automatically opening the electronic remote clamp in response to reaching the speed threshold for the speed of the centrifugal pump, if the one or more trigger conditions is based on at least one of blood flow and air bubbles in the blood.

Example 20 is the method of Example 19, including the opening of the electronic remote clamp and, after a predetermined period, automatically switching between the speed control mode and the flow control mode.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
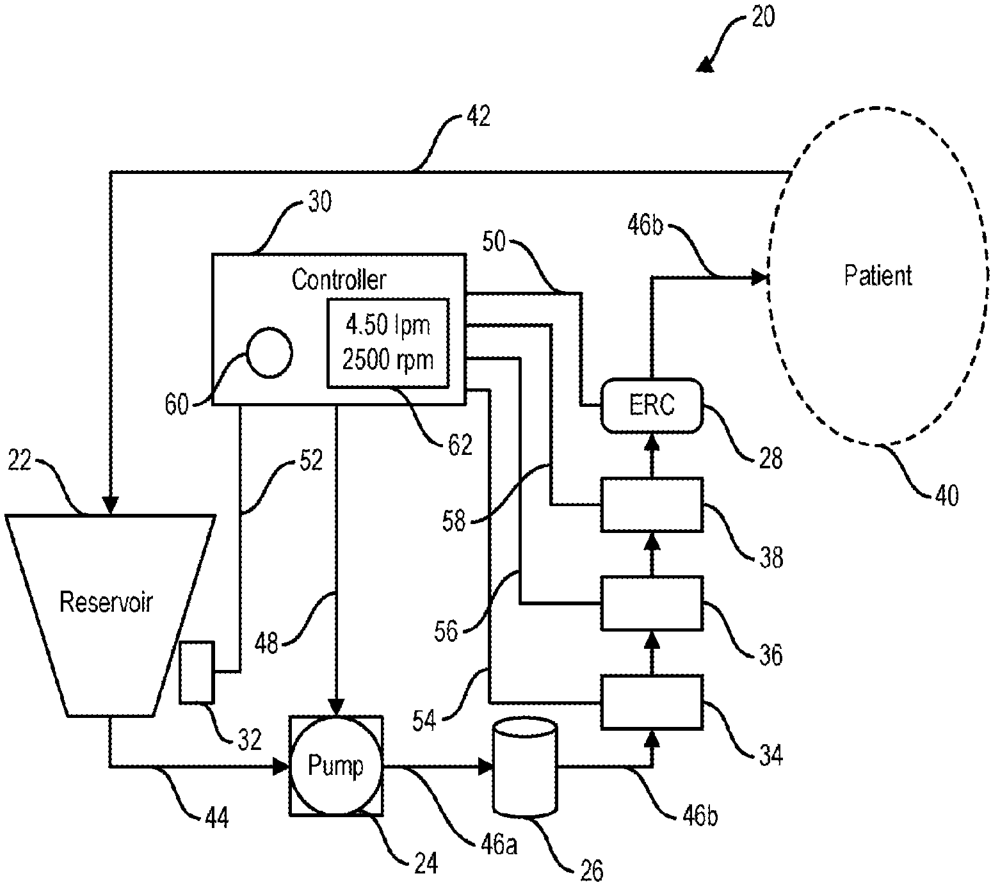
FIG. 1 is a diagram illustrating a system for regulating blood flow in extracorporeal circulation, in accordance with embodiments of the subject matter of the disclosure.

While the disclosure is amenable to various modifications and alternative forms, specific embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the appended claims.

DETAILED DESCRIPTION

FIG. 1 is a diagram illustrating a system 20 for regulating blood flow in extracorporeal circulation, in accordance with embodiments of the subject matter of the disclosure. The system 20 includes a blood reservoir 22, a centrifugal pump 24, an oxygenator 26, an ERC 28, and a controller 30. Also, the system 20 includes a blood level sensor 32, a blood flow sensor 34, a blood pressure sensor 36, and an air bubble sensor 38. In embodiments, the system 20 is part of an HLM.

The blood reservoir 22 is fluidly coupled to receive blood from a patient 40 through blood supply line 42, where the blood is drained from the patient 40 and collected in the blood reservoir 22 through the blood supply line 42.

The centrifugal pump 24 is fluidly coupled to receive blood from the blood reservoir 22 through blood supply line 44. In addition, the centrifugal pump 24 is fluidly coupled to the oxygenator 26 by arterial blood flow line 46*a* and the oxygenator 26 is fluidly coupled to the patient 40 through arterial blood flow line 46*b*. Collectively, the blood supply line 44 and the arterial blood flow lines 46*a* and 46*b* define a blood flow path. In various embodiments, the various blood supply and flow lines are formed of tubing. The centrifugal pump 24 generates blood flow and blood pressure in the system 20. The centrifugal pump 24 is configured to pump the blood from the blood reservoir 22 and through the blood flow lines 46*a* and 46*b* to the oxygenator 26 and back to the patient 40. The ERC 28 is disposed at a location along the blood flow path, including any location on the blood supply line 44 or the arterial blood flow lines 46*a* and 46*b*, and is configured to regulate flow of blood back to the patient by occluding (or partially occluding) the blood flow pathway. In various embodiments, the ERC 28 is coupled to the blood flow line 46*b* and configured to regulate blood flow back to the patient 40. In embodiments, the ERC 28 is configured to fully occlude and fully release the arterial blood flow line 46*b*.

The oxygenator 26 conditions the blood. Where, conditioning the blood is not limited to exchanging heat with the blood and/or exchanging gases with the blood. Instead, conditioning the blood includes other aspects of conditioning the blood, such as filtering the blood and removing gaseous micro-emboli (GME) from the blood. In some embodiments, the oxygenator 26 conditions the blood by exchanging heat with the blood. In some embodiments, the oxygenator 26 conditions the blood by exchanging gases, such as oxygen and/or carbon dioxide, with the blood. In some embodiments, the oxygenator 26 conditions the blood in other suitable ways.

The controller 30 is communicatively coupled to the centrifugal pump 24 through communications channel 48 and to the ERC 28 through communications channel 50. Also, the controller 30 is communicatively coupled to the level sensor 32 through communications channel 52, to the blood flow sensor 34 through communications channel 54, to the blood pressure sensor 36 through communications channel 56, and to the air bubble sensor 38 through communications channel 58. The blood level sensor 32 senses the blood level/volume in the blood reservoir 22. The blood flow sensor 34 senses the flow rate of the blood to the patient 40 through blood flow line 46*b*. The blood pressure sensor 36 senses the blood pressure generated by the centrifugal pump 24 in the blood flow line 46*b*, and the air bubble sensor 38 detects air bubbles in the blood flow line 46*b*. In embodiments, one or more of the communications channels 48, 50, 52, 54, 56, and 58 can be a hard wired connection. In embodiments, one or more of the communications channels 48, 50, 52, 54, 56, and 58 can be a wireless connection.

The controller 30 is configured to establish and regulate blood flow in the system 20. In embodiments, the controller 30 includes one or more microprocessors or computers and memory that includes executable code for performing the functions of the system 20. In embodiments, the memory may be part of the one or more microprocessors or computers, or memory that is accessible over a network, such as the internet.

The controller 30 is configured to operate in a flow control mode and a speed control mode. The controller 30 includes an operational element 60, such as a turning knob, that is manually manipulated to control or set the blood flow rate in the flow control mode and manually manipulated to control or set the speed of the centrifugal pump 24 in the speed control mode. In some embodiments, the controller 30 is configured to operate the system 20 in a combination of the flow control mode and the speed control mode. In some embodiments, the controller 30 is configured to operate the system 20 in a hybrid mode including flow and speed control aspects.

Also, the controller 30 is configured to receive signals from the blood level sensor 32, the blood flow sensor 34, the blood pressure sensor 36, and the air bubble sensor 38, and to provide one or more trigger conditions in response to one or more of the received signals being outside a corresponding preset operating range. The one or more trigger conditions indicate problems with the system 20, including the blood level in the blood reservoir, negative blood flow or retrograde blood flow, and air bubbles in the blood. Also, in embodiments, if the blood pressure sensor 36 indicates that the blood pressure is higher than a preset high value, the controller 30 maintains the ERC 28 open and reduces the flow of blood provided by the centrifugal pump 24 until the blood pressure is reduced below the preset high value. In some embodiments, at least one of the one or more trigger conditions is an alarm condition, wherein the system 20 activates an alarm, such as an audio and/or visual alarm, in the system 20 in response to the alarm condition. In some embodiments, the one or more trigger conditions include other operational aspects of the system 20.

The controller 30 includes a display 62 that displays to the user the speed of the centrifugal pump 24 and the flow rate provided by the centrifugal pump 24. In some embodiments, the speed of the centrifugal pump 24 is measured and/or displayed in RPMs. In some embodiments, the flow rate of the blood provided by the centrifugal pump 24 is measured and/or displayed in liters per minute (lpm). In various embodiments, the speed and flow rate are displayed adjacent or otherwise near each other on the display 62.

The controller 30 controls both the centrifugal pump 24 and the ERC 28 in response to manually manipulating the operational element 60 and based on the signals from the blood level sensor 32, the blood flow sensor 34, the blood pressure sensor 36, and the air bubble sensor 38.

In operation, the controller 30 controls the centrifugal pump 24 to operate in flow control mode and provide a constant flow rate of blood to the patient 40. The flow rate is controlled or set by the perfusionist by manually manipulating, such as turning, the operational element 60. If the controller 30 detects one or more trigger conditions, the controller 30: automatically closes the ERC 28 to fully occlude the arterial blood flow line 46*b*; automatically slows the speed of the centrifugal pump 24 to a predetermined, calibrated minimum RPM value that is sufficient to avoid retrograde blood flow; and automatically switches from flow control mode to speed control mode for as long as the trigger condition persists.

After clearing the trigger condition, operation of the system 20 depends on the type of trigger condition that was cleared. After a blood level trigger condition is cleared, the controller 30 automatically ramps up the speed of the centrifugal pump 24 and, after reaching a threshold speed value, the ERC 28 automatically starts opening. In embodiments, the threshold speed value, which may be an RPM threshold speed value, is predetermined and greater than the above-mentioned minimum RPM value.

After a flow trigger condition or an air bubble trigger condition is cleared, the speed of the centrifugal pump 24 is ramped up by manually manipulating, such as by turning, the operational element 60, such that after reaching a threshold speed value the ERC 28 automatically starts opening. In embodiments, the threshold speed value, which may be an RPM threshold speed value, is predetermined and greater than the above-mentioned minimum RPM value. Also, in embodiments, the threshold speed value is the same for the blood level trigger condition, the blood flow trigger condition, and the air bubble trigger condition.

In each situation, increasing the speed of the centrifugal pump 24 to be greater than the threshold value, automatically starts the opening of the ERC 28. Also, after the ERC 28 is in the fully open condition, and the controller 30 automatically switches from the speed control mode to the flow control mode. In embodiments, the controlled blood flow value is the same as the blood flow value provided prior to the trigger condition, such as a blood level trigger condition. In embodiments, the controlled blood flow value is the blood flow value set by the operational element 60 at the time the ERC 28 is fully opened, such as after blood flow and air bubble trigger conditions.

Thus, the only manual action required by the user in operating the centrifugal pump 24 and the ERC 28, is to manipulate, such as by turning, the operational element 60 to increase or decrease the speed of the centrifugal pump 24 or the blood flow provided by the centrifugal pump 24. System 20 does not require buttons for choosing between the flow control mode and the speed control mode nor does it require buttons for opening and closing the ERC. This greatly simplifies operation of the system 20 in comparison to previous systems. In various embodiments, however, the system 20 does includes buttons for other purposes, including for example, a button to be used only in speed control mode and/or a button to open the ERC to perform retrograde autologous priming (RAP). In various embodiments, such buttons are not visible in the primary display of the touch screen, but rather in subordinate windows of the touch screen.

Figure 2:
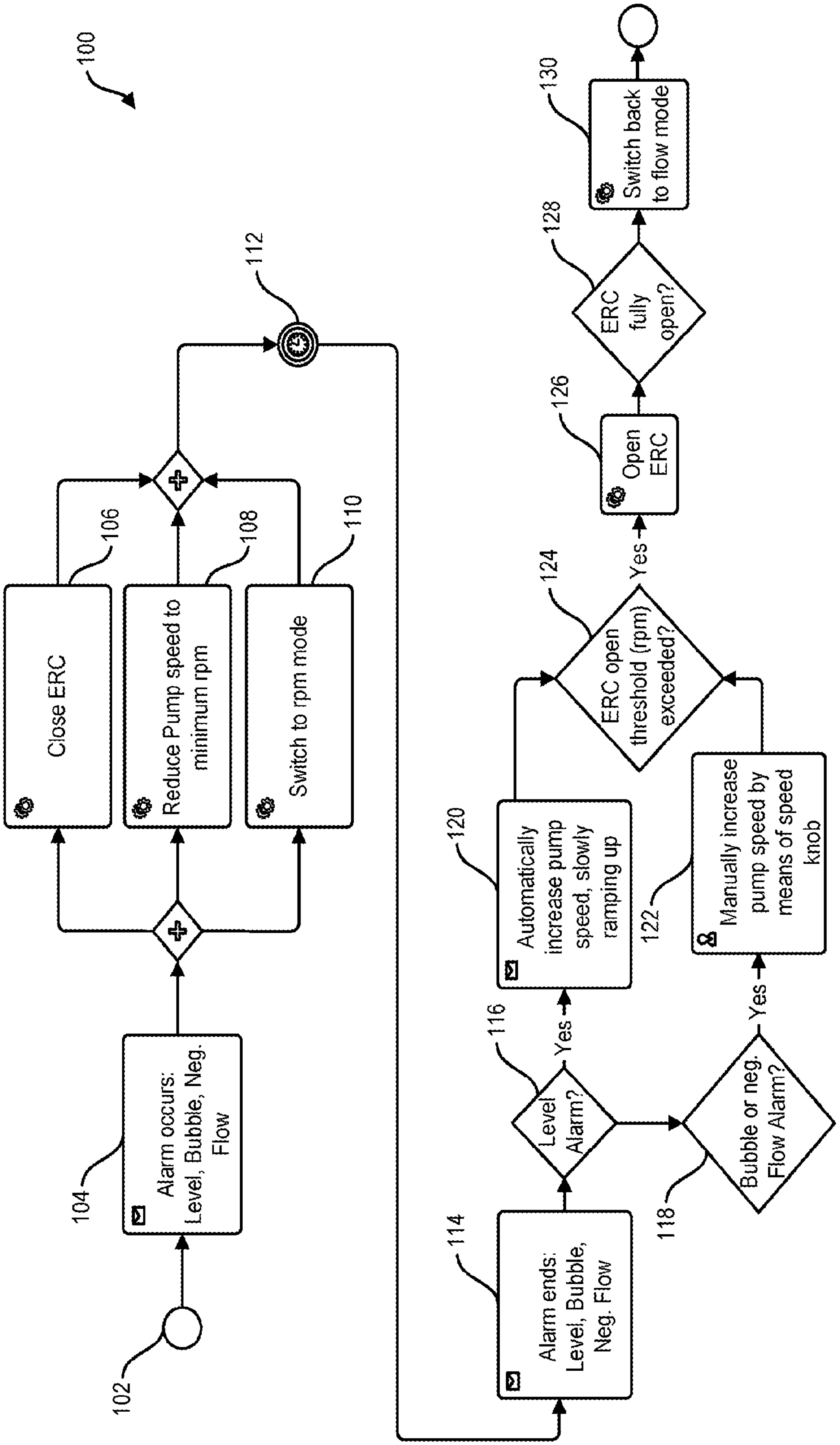
FIG. 2 is a flow chart diagram illustrating operations of the system, in accordance with embodiments of the subject matter of the disclosure.

FIG. 2 is a flow chart diagram 100 illustrating operation of the system 20, in accordance with embodiments of the subject matter of the disclosure. At 102, in operation without trigger conditions, the system 20 operates in flow control mode. The controller 30 controls the centrifugal pump 24 and the ERC 28 to maintain a constant blood flow rate to the patient 40. The controller 30 acts on the speed of the centrifugal pump 24 to maintain the constant blood flow rate through the blood flow lines 46*a* and 46*b* and the controller 30 keeps the ERC 28 open.

At 104, one or more trigger conditions occur, including one or more of a blood level trigger condition, a negative blood flow or retrograde blood flow trigger condition, and an air bubble trigger condition. The air bubble trigger condition includes detecting air bubbles in the arterial blood flow line 46*b*. The blood level trigger condition includes a low level/volume in the venous reservoir 22. The blood flow trigger condition includes negative or retrograde blood flow being measured in the blood flow line 46*b*, where the negative or retrograde blood flow can be caused by stopping or almost stopping the centrifugal pump 24 and/or by a gravity gradient, such as where the patient 40 is higher than the centrifugal pump 24.

In response to the one or more trigger conditions at 104, the controller 30: at 106, automatically closes the ERC 28 to fully occlude the arterial blood flow line 46*b*; at 108, automatically reduces or slows the speed of the centrifugal pump 24 to a minimum RPM value that is sufficient to avoid retrograde blood flow; and, at 110, automatically switches from flow control mode to speed control mode for as long as the trigger condition persists.

After a period, indicated at 112, the trigger condition is cleared or ends at 114 and the system 20 further responds to the trigger condition. At 116, the controller 30 determines whether the trigger condition was a blood level trigger condition and, at 118, the controller 30 determines whether the trigger condition was a blood flow trigger condition or an air bubble trigger condition.

At 120, if the trigger condition was a blood level trigger condition, the controller 30 automatically increases the speed of the centrifugal pump 24, slowly ramping the speed higher. At 122, if the trigger condition was a blood flow trigger condition or an air bubble trigger condition, the speed of the centrifugal pump 24 is manually increased by manipulating the operational element 60, such as by turning a knob.

At 124, the controller 30 determines whether the speed of the centrifugal pump 24 exceeds a pre-set speed threshold value, which may be a pre-set speed threshold value, that is greater than the above minimum RPM value. At 126, if the speed of the centrifugal pump 24 exceeds the pre-set speed threshold value, the controller 30 automatically begins to open the ERC 28 from the fully closed position toward the fully open condition.

At 128, after a pre-set time delay, the controller 30 determines whether the ERC 28 is fully open and, at 130, the controller 30 automatically switches the system 20 from speed control mode to flow control mode. In embodiments, where the trigger condition was a blood level trigger condition, the controlled flow rate coincides with the pre-trigger value. In embodiments, where the trigger condition was a blood flow trigger condition or an air bubble trigger condition, the controlled flow rate is established by the manual action on the operational element 60 at the point in time when the ERC 28 is fully opened.

The advantages provided by the system 20, including the automated way of handling the centrifugal pump 24 and the ERC 28, is evident in terms of easier and user friendlier operations, as compared to previous systems. The user only acts to set the speed of the centrifugal pump 24 or the blood flow rate provided by the centrifugal pump 24. Fastidious calibrations of the low speed or minimum RPM value of the centrifugal pump 24 in alarm, manual transitions between speed control mode and flow control mode, and manual openings of the ERC 28 after an alarm, are no longer required by the user.

Figure 3:
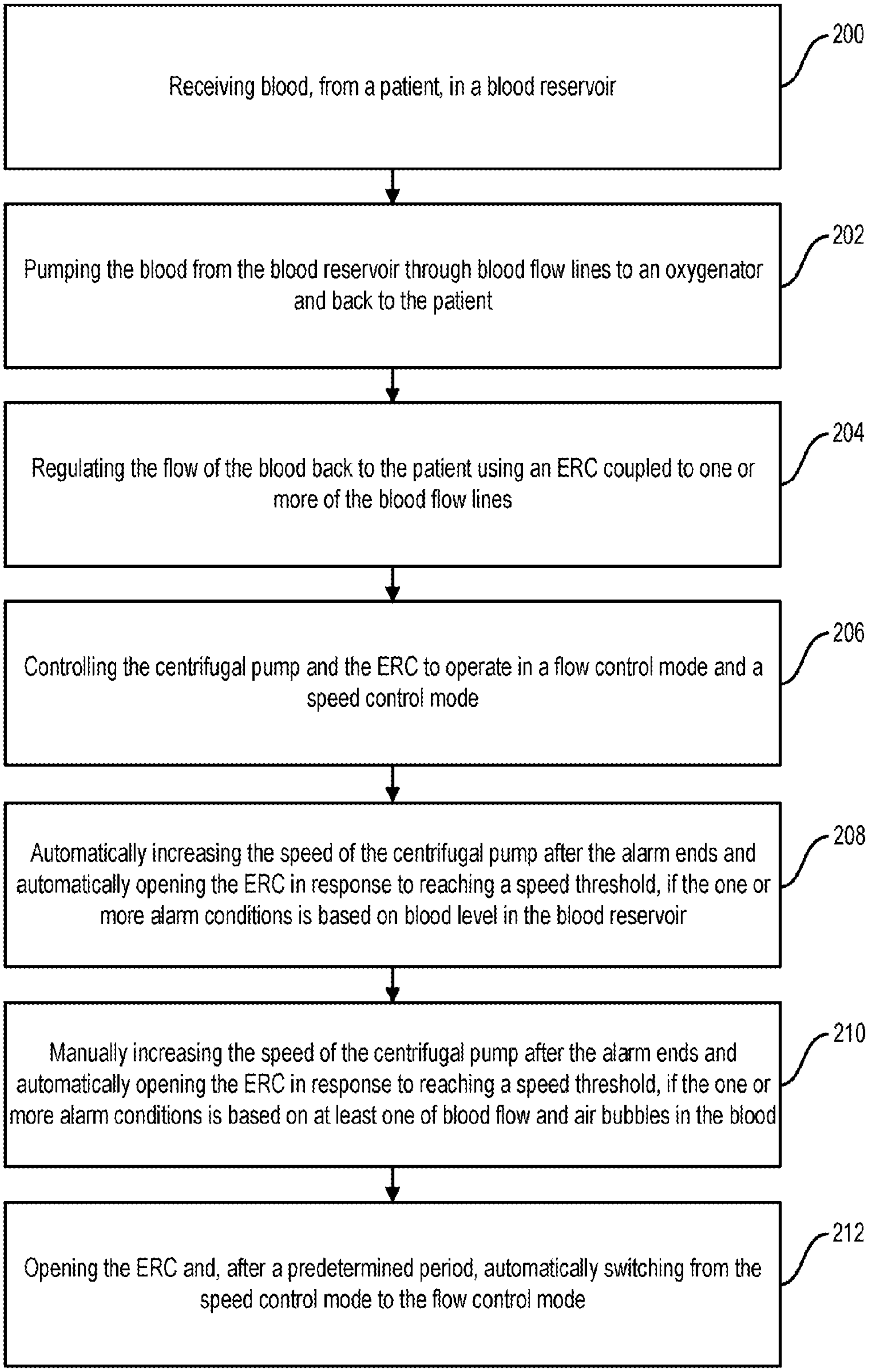
FIG. 3 is a flow chart diagram illustrating a method of regulating blood flow in an extracorporeal circulation system, in accordance with embodiments of the subject matter of the disclosure.

FIG. 3 is a flow chart diagram illustrating a method of regulating blood flow in an extracorporeal circulation system, such as system 20, in accordance with embodiments of the subject matter of the disclosure.

At 200, the method includes receiving blood, from a patient, in a blood reservoir and, at 202, the method includes pumping the blood from the blood reservoir along a blood flow path through blood flow lines to an oxygenator and back to the patient using a centrifugal pump. At 204, the method includes regulating the flow of the blood back to the patient using an ERC coupled along the blood flow path, to one or more of the blood flow lines. In various embodiments, regulating includes occluding or completely stopping blood flow along the blood flow path.

At 206, the method includes controlling, using a controller, the centrifugal pump and the ERC to operate in a flow control mode and a speed control mode, where the controller is configured to automatically switch from the flow control mode to the speed control mode in response to one or more trigger conditions, and the controller is configured to automatically switch from the speed control mode to the flow control mode in response to opening the ERC.

Also, in embodiments, in response to the one or more trigger conditions, the method includes automatically closing the ERC and automatically reducing the speed of the centrifugal pump. And, in embodiments, the method includes receiving signals from one or more of a blood flow sensor, an air bubble sensor, and a blood level sensor and providing the one or more trigger conditions based on the signals received from the one or more of the blood flow sensor, the air bubble sensor, and the blood level sensor signals.

At 208, the method includes automatically increasing the speed of the centrifugal pump after the trigger condition ends and automatically opening the ERC in response to reaching a speed threshold for the speed of the centrifugal pump, if the one or more trigger conditions is based on blood level in the blood reservoir.

At 210, the method includes manually increasing the speed of the centrifugal pump after the trigger condition ends and automatically opening the ERC in response to reaching a speed threshold for the speed of the centrifugal pump, if the one or more trigger conditions is based on at least one of blood flow and air bubbles in the blood. Where, manually increasing the speed includes manually manipulating an operational element, such as a turning knob.

At 212, the method includes opening the ERC and automatically switching from the speed control mode to the flow control mode. In some embodiments, this automatic switching occurs a predetermined period after opening of the ERC.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for regulating blood flow in extracorporeal circulation, comprising:

- a blood reservoir configured to receive blood from a patient;
- an oxygenator configured to condition the blood from the patient;
- a centrifugal pump fluidly coupled to the blood reservoir and the oxygenator and configured to pump the blood from the blood reservoir along a blood flow path to the oxygenator and back to the patient;
- an electronic remote clamp disposed at a location along the blood flow path and configured to regulate flow of the blood back to the patient; and
- a controller configured to operate in a flow control mode and a speed control mode and including an operational element configured to set a blood flow value in the flow control mode and to set a speed of the centrifugal pump in the speed control mode, wherein the controller is configured to automatically switch between the flow control mode and the speed control mode in response to one or more trigger conditions and to automatically switch between the speed control mode and the flow control mode in response to opening the electronic remote clamp.

2. The system of claim 1, wherein the controller is configured to automatically close the electronic remote clamp, reduce the speed of the centrifugal pump, and switch operation to the speed control mode in response to the one or more trigger conditions.

3. The system of claim 2, wherein the one or more trigger conditions indicate one of a retrograde blood flow condition, air bubbles in the blood, and a blood level in the blood reservoir.

4. The system of claim 3, wherein the controller is configured to receive signals from a blood flow sensor, an air bubble sensor, and a blood level sensor and to provide the one or more trigger conditions based on the blood flow sensor, the air bubble sensor, and the blood level sensor signal.

5. The system of claim 1, wherein if the one or more trigger conditions is based on blood level in the blood reservoir, the controller is configured to automatically increase the speed of the centrifugal pump after the one or more trigger conditions ends and to automatically begin opening the electronic remote clamp in response to reaching a speed threshold for the speed of the centrifugal pump.

6. The system of claim 5, wherein the controller is configured to continue opening the electronic remote clamp and, after a predetermined period, automatically switch to the flow control mode.

7. The system of claim 1, wherein if the one or more trigger conditions is based on at least one of a retrograde blood flow and air bubbles in the blood, the speed of the centrifugal pump is changed by user manipulation of the operational element and the electronic remote clamp begins to open in response to the speed of the centrifugal pump reaching a speed threshold, such that the controller is configured to control the centrifugal pump and the electronic remote clamp in response to user manipulation of the operational element.

8. The system of claim 7, wherein the controller is configured to continue opening the electronic remote clamp and, after a predetermined period, automatically switch to the flow control mode.

9. A system for regulating blood flow in extracorporeal circulation, comprising:

- an oxygenator configured to receive and condition blood from a patient;
- a centrifugal pump fluidly coupled to the oxygenator and configured to pump the blood from the oxygenator along a blood flow path back to the patient;
- an electronic remote clamp coupled at a location along the blood flow path and configured to regulate flow of the blood back to the patient; and
- a controller configured to operate in a flow control mode and a speed control mode, wherein the controller is configured to automatically close the electronic remote clamp and reduce the speed of the centrifugal pump and switch between the flow control mode and the speed control mode in response to one or more trigger conditions, and to automatically begin opening the electronic remote clamp in response to the speed of the centrifugal pump being increased to a speed threshold.

10. The system of claim 9 further comprising a blood reservoir configured to receive and hold blood from the patient, wherein the centrifugal pump is fluidly coupled to the blood reservoir and the oxygenator and configured to pump the blood from the blood reservoir through blood flow lines along the blood flow path to the oxygenator and back to the patient.

11. The system of claim 9, wherein the controller is configured to continue opening the electronic remote clamp and automatically switch between the speed control mode and the flow control mode.

12. The system of claim 10, wherein if the one or more trigger conditions is based on blood level in the blood reservoir, the controller is configured to automatically increase the speed of the centrifugal pump to the speed threshold after the one or more trigger conditions ends.

13. The system of claim 9, comprising an operational element configured to set a blood flow value in the flow control mode and to set a speed of the centrifugal pump in the speed control mode, wherein if the one or more trigger conditions is based on at least one of a retrograde blood flow and air bubbles in the blood, the speed of the centrifugal pump is increased to the speed threshold by user manipulation of the operational element.

14. A method of regulating blood flow in an extracorporeal circulation system, comprising:

receiving blood, from a patient, in a blood reservoir;

pumping the blood from the blood reservoir along a blood flow path to an oxygenator and back to the patient using a centrifugal pump;

regulating flow of the blood back to the patient using an electronic remote clamp coupled at a location along the blood flow path; and controlling, using a controller, the centrifugal pump and the electronic remote clamp to operate in a flow control mode and a speed control mode, wherein controlling the centrifugal pump and the electronic remote clamp includes:

automatically switching between the flow control mode and the speed control mode in response to one or more trigger conditions; and automatically switching between the speed control mode and the flow control mode in response to opening the electronic remote clamp.

15. The method of claim 14, comprising automatically closing the electronic remote clamp and automatically reducing the speed of the centrifugal pump in response to the one or more trigger conditions.

16. The method of claim 14, comprising receiving signals from a blood flow sensor, an air bubble sensor, and a blood level sensor and providing the one or more trigger conditions based on the signals from the blood flow sensor, the air bubble sensor, and the blood level sensor.

17. The method of claim 14, comprising automatically increasing the speed of the centrifugal pump after the one or more trigger conditions ends and automatically opening the electronic remote clamp in response to reaching a speed threshold for the speed of the centrifugal pump, if the one or more trigger conditions is based on blood level in the blood reservoir.

18. The method of claim 17, comprising the opening of the electronic remote clamp and, after a predetermined period, automatically switching between the speed control mode and the flow control mode.

19. The method of claim 14, comprising using an operational element to set a blood flow value in the flow control mode and to set a speed of the centrifugal pump in the speed control mode, and changing the speed of the centrifugal pump to reach a speed threshold for the speed of the centrifugal pump by manually manipulating the operational element and automatically opening the electronic remote clamp in response to reaching the speed threshold for the speed of the centrifugal pump, if the one or more trigger conditions is based on at least one of blood flow and air bubbles in the blood.

20. The method of claim 19, comprising the opening of the electronic remote clamp and, after a predetermined period, automatically switching from the speed control mode to the flow control mode.

* * * * *